US011537702B2

(12) United States Patent
Shute et al.

(10) Patent No.: US 11,537,702 B2
(45) Date of Patent: Dec. 27, 2022

(54) IMPLANTED MEDICAL DEVICE AUTHENTICATION BASED ON COMPARISON OF INTERNAL IMU SIGNAL TO EXTERNAL IMU SIGNAL

(71) Applicant: Cardiac Pacemakers, Inc., St. Paul, MN (US)

(72) Inventors: Jonathan Bennett Shute, Eagan, MN (US); Bin Mi, Arden Hills, MN (US); Andrew Bomett, Inver Grove Heights, MN (US); Michael Sheehan Seeberger, Afton, MN (US); Grace Ann Wiechman, Minneapolis, MN (US); Kenneth P. Hoyme, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 349 days.

(21) Appl. No.: 16/870,435

(22) Filed: May 8, 2020

(65) Prior Publication Data
US 2020/0364327 A1 Nov. 19, 2020

Related U.S. Application Data

(60) Provisional application No. 62/847,074, filed on May 13, 2019.

(51) Int. Cl.
*G06F 21/44* (2013.01)
*G06F 3/01* (2006.01)
(Continued)

(52) U.S. Cl.
CPC ............ *G06F 21/44* (2013.01); *A61B 5/0022* (2013.01); *A61B 5/0031* (2013.01); *G06F 3/017* (2013.01);
(Continued)

(58) Field of Classification Search
CPC ....... G06F 21/44; G06F 3/017; A61B 5/0022; A61B 5/0031; A61B 2562/0219;
(Continued)

(56) References Cited

U.S. PATENT DOCUMENTS 5,935,078 A 8/1999 Freierbach
6,223,018 B1 4/2001 Fukumoto et al.
(Continued)

FOREIGN PATENT DOCUMENTS

EP 2438959 4/2012
WO 2016133813 8/2016
(Continued)

OTHER PUBLICATIONS

Challa, Sravani et al., "Authentication Protocols for Implantable Medical Devices: Taxonomy, Analysis and Future Directions," IEEE Consumer Electronics Magazine vol. 7, No. 1, Jan. 1, 2018 pp. 57-65 (9 pages).
(Continued)

*Primary Examiner* — David D Davis
(74) *Attorney, Agent, or Firm* — Pauly, DeVries Smith & Deffner LLC

(57) ABSTRACT

Embodiments herein relate to sensor based authentication between an implantable medical device (IMD) and an external device. In an embodiment, the IMD includes a wireless communication module and an internal inertial measurement unit (IMU) capable of measuring vibrations, movement, or rotation. The IMD is configured to record an internal IMU signal from the internal IMU. The external device includes a wireless communication module and an external IMU. The external device is configured to record an external IMU signal from the external IMU. The system further includes a data processing system to receive a first level communication that can include the internal IMU
(Continued)

signal, the external IMU signal, or both, compare data from the internal IMU signal with data from the external IMU signal, and authorize a second level communication based on results of the comparison step.

20 Claims, 9 Drawing Sheets

(51) Int. Cl.
- *G16H 40/67* (2018.01)
- *A61B 5/00* (2006.01)
- *H04W 4/38* (2018.01)

(52) U.S. Cl.
CPC .............. *G16H 40/67* (2018.01); *H04W 4/38* (2018.02); *A61B 2562/0219* (2013.01)

(58) Field of Classification Search
CPC ........ A61B 5/686; G16H 40/67; G16H 10/60; H04W 4/38
See application file for complete search history.

(56) References Cited

U.S. PATENT DOCUMENTS

| | | | |
|---|---|---|---|
| 6,277,078 | B1 | 8/2001 | Porat et al. |
| 6,336,903 | B1 | 1/2002 | Bardy |
| 6,368,284 | B1 | 4/2002 | Bardy |
| 6,398,728 | B1 | 6/2002 | Bardy |
| 6,411,840 | B1 | 6/2002 | Bardy |
| 6,440,066 | B1 | 8/2002 | Bardy |
| 6,764,446 | B2 | 7/2004 | Wolinsky et al. |
| 7,425,200 | B2 | 9/2008 | Brockway et al. |
| 10,682,517 | B2 | 6/2020 | Hoffman et al. |
| 11,110,281 | B2 | 9/2021 | Mi et al. |
| 2002/0077673 | A1 | 6/2002 | Penner et al. |
| 2002/0082480 | A1 | 6/2002 | Riff et al. |
| 2002/0177782 | A1 | 11/2002 | Penner |
| 2005/0021370 | A1 | 1/2005 | Riff et al. |
| 2009/0048644 | A1 | 2/2009 | Stahmann et al. |
| 2013/0217998 | A1* | 8/2013 | Mahfouz .............. A61B 5/002 600/595 |
| 2014/0273824 | A1 | 9/2014 | Fenner et al. |
| 2016/0213937 | A1 | 7/2016 | Reinke et al. |
| 2018/0146374 | A1 | 5/2018 | Golan et al. |
| 2019/0083039 | A1 | 3/2019 | Shute et al. |
| 2019/0083041 | A1 | 3/2019 | Shute et al. |
| 2019/0201702 | A1 | 7/2019 | Mi et al. |
| 2021/0370075 | A1 | 12/2021 | Mi et al. |

FOREIGN PATENT DOCUMENTS

| | | |
|---|---|---|
| WO | 2017189187 | 11/2017 |
| WO | 2019136233 | 7/2019 |

OTHER PUBLICATIONS

Ferguson, John E. et al., "Wireless communication with implanted medical devices using the conductive properties of the body," Expert Rev Med Devices. Jul. 2011; 8(4): 427-433 (14 pages).

Heather, Kenedi et al., "A Novel Authentication Biometric for Pacemakers," Presentation, 2018 IEEE/ACM International Conference on Connected Health: Applications, Systems and Engineering Technologies (CHASE), Sep. 26-28, 2018, Washington, DC, USA (7 pages).

"International Preliminary Report on Patentability," for PCT Application No. PCT/US2019/012328 dated Jul. 16, 2020 (10 pages).

"International Search Report and Written Opinion," for PCT Application No. PCT/US2019/012328 dated Apr. 16, 2019 (14 pages).

Marin, Eduard et al., "A Survey on Physiological-signal-based security for medical devices," International Association for Cryptologic Research vol. 20160910:154345, Sep. 6, 2016 pp. 1-16 (16 pages).

Rushanan, Michael et al., "SoK: Security and Privacy in Implantable Medical Devices and Body Area Networks," 2014 IEEE Symposium on Security and Privacy (16 pages).

"Non-Final Office Action," for U.S. Appl. No. 16/239,395 dated Dec. 15, 2020 (15 pages).

"Response to Non Final Office Action," for U.S. Appl. No. 16/239,395, filed Mar. 8, 2021 (10 pages).

* cited by examiner

IMPLANTED MEDICAL DEVICE AUTHENTICATION BASED ON COMPARISON OF INTERNAL IMU SIGNAL TO EXTERNAL IMU SIGNAL

This application claims the benefit of U.S. Provisional Application No. 62/847,074 filed May 13, 2019, the content of which is herein incorporated by reference in its entirety.

BACKGROUND

Many implantable medical devices (IMDs) have significant onboard data storage capabilities. Sensitive patient data is included in the onboard data of many IMDs, as well as valuable and useful patient data. Many IMDs have functions that are life-saving, important to patient health, important to diagnosis, or multiple of these functions. Security of the data on IMDs and control of IMDs is a high priority. The ability to appropriately access the onboard data of an IMD and appropriately control the IMD are competing high priorities.

SUMMARY

In a first aspect, a system for authenticating communication between an implantable medical device (IMD) for implantation in a patient and an external device includes the IMD capable of being implanted into a patient's body. The IMD includes a wireless communication module and an internal inertial measurement unit (IMU). The internal IMU is capable of measuring vibrations, movement, or rotation. The IMD is configured to record an internal IMU signal from the internal IMU. The system includes the external device located externally to the patient's body. The external device includes a wireless communication module and an external IMU capable of measuring vibrations, movement, or rotation. The external device is configured to record an external IMU signal from the external IMU. The system further includes a data processing system that includes computer instructions stored in memory to: receive a first level communication that can include the internal IMU signal, the external IMU signal, or both, compare data from the internal IMU signal with data from the external IMU signal, and authorize a second level communication based on results of the comparison step.

In a second aspect, in addition to one or more of the preceding or following aspects, or in the alternative to some aspects, the data processing system further includes computer instructions stored in memory to synchronize the internal IMU signal and the external IMU signal.

In a third aspect, in addition to one or more of the preceding or following aspects, or in the alternative to some aspects, synchronizing further includes comparing a timestamp of the internal IMU signal to a timestamp of the external IMU signal.

In a fourth aspect, in addition to one or more of the preceding or following aspects, or in the alternative to some aspects, synchronizing further includes comparing a fiducial from the internal IMU signal with a fiducial of the external IMU signal.

In a fifth aspect, in addition to one or more of the preceding or following aspects, or in the alternative to some aspects, the fiducial from the internal IMU signal is a signal peak and the fiducial from the external IMU signal is a signal peak.

In a sixth aspect, in addition to one or more of the preceding or following aspects, or in the alternative to some aspects, the data processing system is located in the IMD and receives the external IMU, located in the external device and receives the internal IMU, or located in an external server and receives the internal IMU and the external IMU.

In a seventh aspect, in addition to one or more of the preceding or following aspects, or in the alternative to some aspects, the external device is a mobile device, a cellular telephone, a wearable device, or a combination of these.

In an eighth aspect, in addition to one or more of the preceding or following aspects, or in the alternative to some aspects, the internal IMU includes an accelerometer, a gyroscope, or a magnetometer and wherein the external IMU includes an accelerometer, a gyroscope, or a magnetometer.

In a ninth aspect, in addition to one or more of the preceding or following aspects, or in the alternative to some aspects, the comparison step includes comparing the internal IMU signal with the external IMU signal or comparing data derived from internal IMU signal with data derived from the external IMU signal.

In a tenth aspect, in addition to one or more of the preceding or following aspects, or in the alternative to some aspects, the data processing system derives a heart sound signal, a heart rate signal, a posture signal, a respiration signal, an external device vibration signal, or a tap signal from the internal IMU signal and the external IMU signal.

In an eleventh aspect, in addition to one or more of the preceding or following aspects, or in the alternative to some aspects, the second level of communication includes secure data, patient data, instructions, commands, software updates, firmware updates, or a combination of these.

In a twelfth aspect, a method for authenticating communication between an implantable medical device (IMD) and an external device is described. The IMD is capable of being implanted into a patient's body and includes a wireless communication module and an internal inertial measurement unit (IMU). The external device is located externally to the patient's body and includes a wireless communication module and an external IMU. The method includes recording an internal IMU signal from the internal IMU, recording an external IMU signal from the external IMU, receiving a first level communication that can include the internal IMU signal, the external IMU signal, or both, comparing data from the internal IMU signal with data from the external IMU signal, and authorizing a second level communication based on results of the comparison step.

In a thirteenth aspect, in addition to one or more of the preceding or following aspects, or in the alternative to some aspects, the IMD is implanted in the patient's body and the method further can include placing the external device in contact with the patient's body.

In a fourteenth aspect, in addition to one or more of the preceding or following aspects, or in the alternative to some aspects, the method further can include initiating a second level communication session by sending a request from the external device to the IMD.

In a fifteenth aspect, in addition to one or more of the preceding or following aspects, or in the alternative to some aspects, the method further can include synchronizing the internal IMU signal and the external IMU signal.

In a sixteenth aspect, in addition to one or more of the preceding or following aspects, or in the alternative to some aspects, synchronizing further includes comparing a timestamp of the internal IMU signal to a timestamp of the external IMU signal, comparing a fiducial from the internal IMU signal with a fiducial of the external IMU signal, or comparing a signal peak from the internal IMU signal with a signal peak from the external IMU signal.

In a seventeenth aspect, in addition to one or more of the preceding or following aspects, or in the alternative to some aspects, a data processing system performs the step of receiving and is located in the IMD and receives the external IMU, is located in the external device and receives the internal IMU, or is located in an external server and receives the internal IMU and the external IMU.

In an eighteenth aspect, in addition to one or more of the preceding or following aspects, or in the alternative to some aspects, comparing includes comparing the internal IMU signal with the external IMU signal, or comparing data derived from internal IMU signal with data derived from the external IMU signal.

In a nineteenth aspect, in addition to one or more of the preceding or following aspects, or in the alternative to some aspects, the method further can include deriving a heart sound signal, a heart rate signal, a posture signal, a respiration signal, an external device vibration signal, or a tap signal from the internal IMU signal and from the external IMU signal.

In a twentieth aspect, in addition to one or more of the preceding or following aspects, or in the alternative to some aspects, the method includes, after the second level of communication is authorized, sending secure data, patient data, instructions, commands, software updates, firmware updates, or a combination of these to or from the IMD.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following FIGS.

Figure 1:
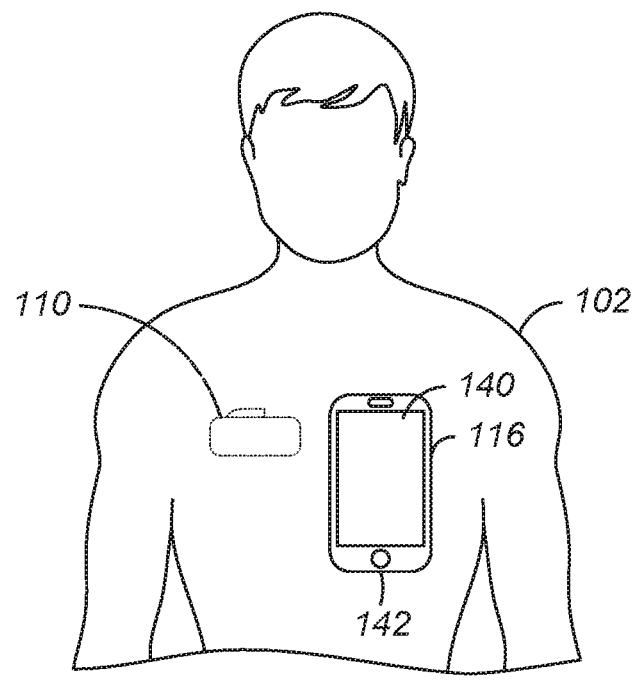
FIG. 1 is a schematic view of a patient having an IMD and an external device placed in contact with the patient's body during an authentication process in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

A system and method for authenticating communication between an implantable medical device (IMD) capable of implantation in a patient and an external device is described herein. The system and method take advantage of the fact that many IMDs and common electronic devices, such as cell phones, include inertial measurement units (IMUs) capable of measuring vibrations, movement or rotation. Examples of IMUs include accelerometers, gyroscopes, and magnetometers.

During the authentication process, an external device is placed near to, such as in contact with or very close to the patient's body. The external device may be placed over a location of an IMD implanted in the patient, for example. An internal IMU of the IMD generates an internal IMU signal, while at the same time, an external IMU of the external device generates an external IMU signal. The two IMU signals may contain data or be processed to reveal data about physiological processes taking place within the body, such as heart sounds or respiration rate. The two IMU signals may contain data or be processed to reveal data about posture of the patient, physical motion of the patient, or a tapping sequence performed on the patient's body.

A data processing system then compares data from the internal IMU signal to data from the external IMU signal and determines a level of similarity. A close match indicates that the external device is in very close proximity to the patient, such as contacting the patient's body. If the IMU signals match sufficiently, then secure communication is authorized between the IMD and the external device.

A benefit of the system is reducing the likelihood of unauthorized access to an IMD from an external device for malintent, such as for unauthorized activation or deactivation of the device, unauthorized software changes, unauthorized data deletion, unauthorized rewriting of memory, or unauthorized downloading of medical data. Because close proximity of the external device to the patient is a prerequisite for matching signals to be generated by both IMUs, secure communication is unlikely to happen without the patient being aware that a secure communication session is being initiated.

Physiologic signals, such as heart sounds and respiration signals, are affected by a particular patient's anatomy, such as the size, structure and performance of the patient's heart. As a result, many physiological signals are highly variable and difficult to predict. As a further result, it would be very difficult for a person attempting unauthorized access to imitate or guess at an IMU signal that would be generated by an external IMU in close proximity to the patient's body in order to gain access to secure communication. A tapping sequence will also have variability that would be difficult to predict. In some examples, the complex data signal from the two IMUs can be subjected to further processing before a match comparison is performed and secure communication is enabled, thereby further increasing the difficulty of unauthorized secure communication.

The hardware required to execute the authentication process is common. Small, reliable IMUs are commercially available. Many IMDs already contain an IMU or could be modified to contain an IMU. Cell phones commonly include IMUs. Also, when a patient receives an IMD, the patient is frequently provided with an external IMD phone communicator device which already contains an IMU or could be modified to contain an IMU.

Figure 2:
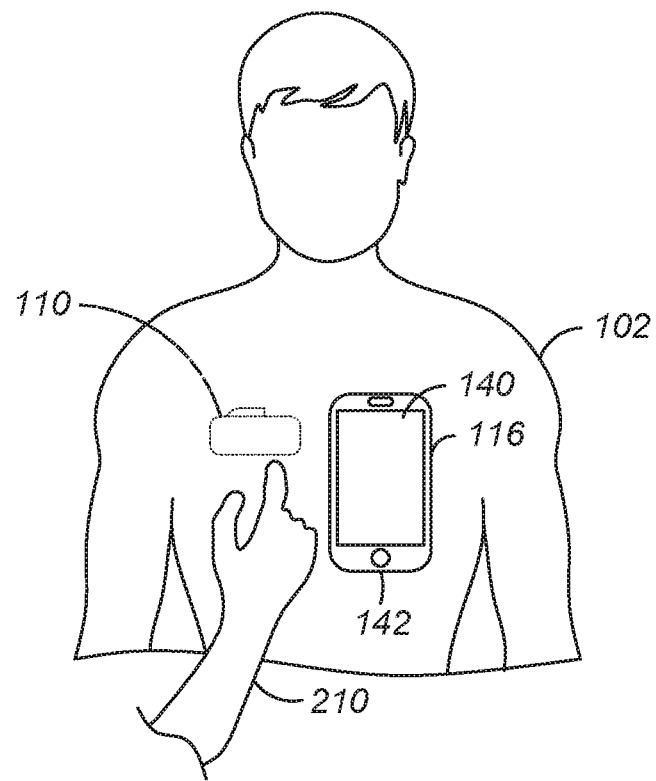
FIG. 2 is a schematic view of a patient having an IMD and an external device placed in contact with the patient's body during a tap sequence authentication process in accordance with various embodiments herein.

System for Authentication of Secure Communication (FIG. 1-2)

FIG. 1 is a schematic view of a system for authenticating communication between an IMD for implantation in a patient and an external device placed near to or in contact with the patient's body during an authentication process in accordance with various embodiments herein. FIG. 1 illustrates an outline of a patient body 102, an IMD 110 implanted in the body 102, and an external device 116. The IMD 110 includes a wireless communication module and an internal IMU capable of measuring vibrations, movement, or rotation. The IMD is configured to record an internal IMU signal from the internal IMU.

The external device 116 is located externally to the patient's body 102 and includes a wireless communication module and an external IMU. The external device is configured to record an external IMU signal generated by the external IMU. The system also includes a data processing system including computer instructions stored in memory to receive a first level communication including the internal IMU signal, the external IMU signal, or both. The data processing system further compares data from the internal IMU signal with data from the external IMU signal and authorizes a second level communication based on results of the comparison step.

The internal IMU and external IMU can detect motion, vibration or rotation generated in a number of different ways, such as by the patient's heart, by the patient's motion, by the patient's respiration, by a tapping motion, or other signal. The data processing system can use the input from the IMUs to generate, reveal, or derive a heart sound signal, a heart rate signal, a posture signal, a respiration signal, an external device vibration signal, a tap signal, or another signal from the internal IMU signal and the external IMU signal.

FIG. 2 is a schematic view of the patient's body 102 having an IMD 110 and an external device 116 placed in contact with the patient's body 102 during the authentication process in accordance with various embodiments herein. A person seeking access to a second level of communication with the IMD performs a tap sequence by using their hand 210, such as by using their finger, to tap on the patient's chest. For example, the person seeking access might tap three times on the patient's chest. The person seeking access may be a clinician, the patient, or a caregiver.

Figure 3:
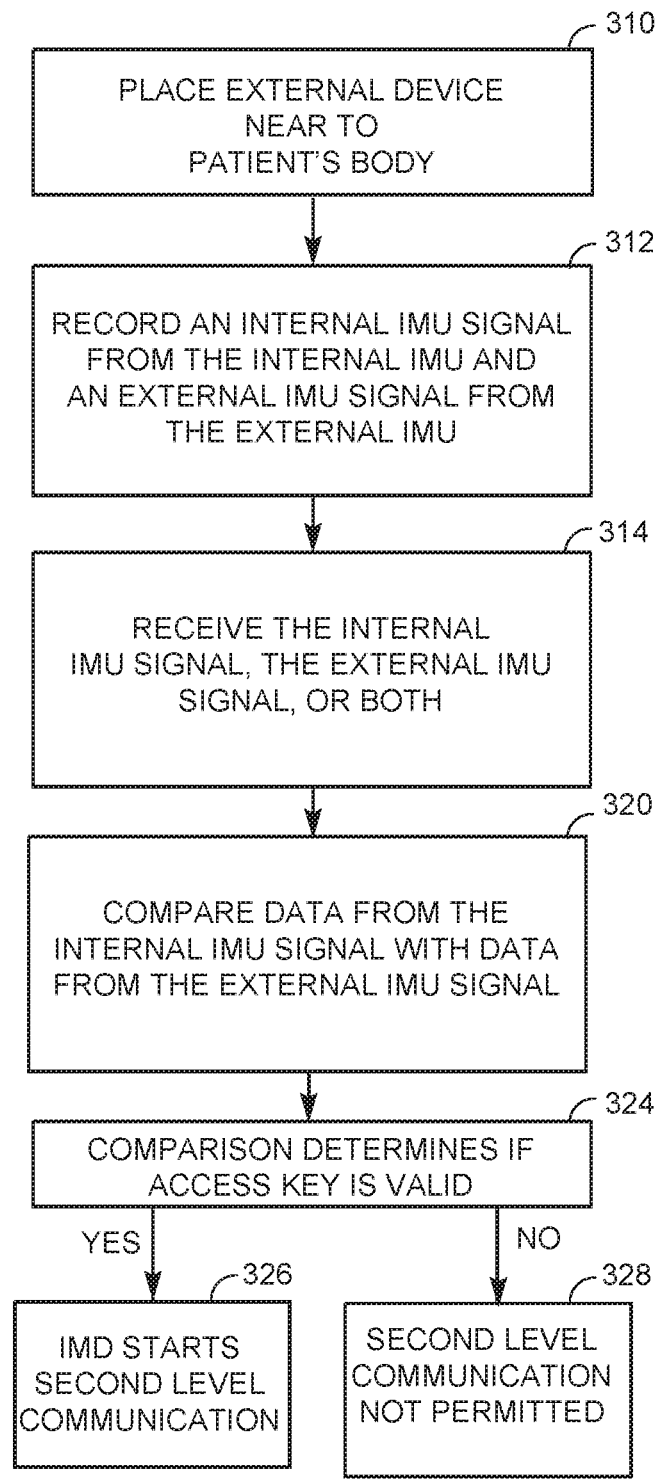
FIG. 3 is a flowchart showing one example of a method of authentication between an IMD and an external device in accordance with various embodiments herein.

Method of Authorized Communication (FIG. 3)

FIG. 3 is a flowchart showing one example of a method of authentication between an IMD and an external device in accordance with various embodiments herein. In a first step 310, the external device 116 is placed near to the patient's body 102. For example, the external device 116 may be in contact with the patient's body, such as laying on the patient's chest. An external device is in contact with the patient's body if the device is touching the patient's body directly or touching the patient's clothing. In various embodiments, during the authentication process, the external device is within 5 centimeters (cm) of the patient's body, within 2 cm of the patient's body, within 1 cm of the patient's body, in contact with the patient's clothing, resting on a part of the patient's body, in contact with the patient's skin, or a combination of these. In addition or in the alternative, the external device may be near to a part of the patient's body that contains the IMD. For example, the external device may be near the patient's chest where the IMD is a cardiac monitor implanted in the patient's chest or near the abdomen where the IMD is an insulin pump implanted in the abdominal cavity.

In step 312, an internal IMU signal is recorded by the internal IMU and an external IMU signal is recorded by the external IMU. This step may be initiated by the external device communicating on an open channel with the IMD to request a second level communication session with the IMD. In one example, the IMD is able to receive a communication-initiating request on the open channel in a low security state in which first level communication is permitted. The communication-initiating request is an example of a first level communication. The communication-initiating request may cause the IMD to enter an authentication phase.

In another example, the IMD is periodically sending communications to see if any other devices desire communication with the IMD. The IMD then listens for a responsive communication for a period of time after the inquiry. During that period of time, the external device can transmit a message to the IMD that second level communication is desired with the IMD.

In another example, a magnet trigger or other external trigger is used to wake-up the IMD so that first level communications are received by the IMD, can be sent by the IMD, or both. An external device such as a cell phone can include the magnet trigger.

Receiving the Internal IMU, the External IMU, or Both

Once the IMD is in a state receptive to receive first level communications, the external device can send a wireless signal, such as a radio-frequency signal, instructing the IMD to record the internal IMU signal. At the same time or approximately the same time, the external device begins recording the external IMU signal. In various examples, the recording of the internal IMU signal may be initiated immediately upon the IMU entering the authentication phase and recording of the external IMU may be simultaneously initiated.

The external IMU signal and the internal IMU signal are recorded for a first period of time. The first period of time may be about 30 seconds, about 10 seconds, less than one minute, at least 2 seconds, at least 5 seconds, at least 10 seconds, combinations of these, or other durations. After the recording of the external IMU and internal IMU have concluded, a data processing system receives a first level communication comprising the internal IMU signal, the external IMU signal, or both at step 314.

In one example, a data processing system located in the external device receives the internal IMU signal via wireless communication from the IMD. Then, the data processing system in the external device may perform the step 320 of comparing data from the internal IMU signal with data from the external IMU signal. Alternatively, the external device could then send both the internal and external IMU signals to an external server for performance of the comparison step 320.

In another example, a data processing system located in the IMD receives the external IMU signal via wireless communication from the external device. In this example, the data processing system in the external device then performs the step 320 of comparing data from the internal IMU signal with data from the external IMU signal.

In yet another example, a data processing system is located in an external server and receives both the internal IMU and the external IMU via wireless communication from the IMD and the external device. In this example, the data processing system in the external server performs the step 320 of comparing data from the internal IMU signal with data from the external IMU signal.

Comparison

The comparison step 320 can include comparing the internal IMU signal with the external IMU signal. Alternatively, instead of comparing the raw IMU signals, the comparing step may include comparing data derived from internal IMU signal with data derived from the external IMU signal. Deriving data from the IMU signals may include the steps of filtering using a high bandpass filter, filtering using a low bandpass filter, offsetting, rectifying a signal, and many other techniques.

The IMU signals can be used to derive a heart sound signal, a heart rate signal, a posture signal, a respiration signal, a tap signal, or other signals, for example. Other examples of data that can be derived are an amplitude of a tap signature, what time did a first tap occur, or other specific parameters of the two IMU signals. In another example, the external device could generate a vibration signal or sequence that is detected by the internal IMU and external IMU. An external device vibration signal can be unique, can be generated randomly, or both, in various embodiments. An external device vibration signal can be distinctive in its frequency change in a sequence, such as including a series of tones at different frequencies and pauses. For example, an external device vibration signal can include a tone at 100 Hz for 2 seconds, then a pause for one second, the a tone at 150 Hz for 2 seconds.

The step of comparing may include calculating a correlation coefficient between a waveform of the data from the internal IMU signal and a waveform of the data from the external IMU signal. In various examples, a correlation coefficient has a value between negative one and one. A value of one indicates a perfect match between the two signals. A value of negative one indicates that one signal is the negative complement of the other signal. This could happen where two IMUs measure the same vibration signal and one IMU oriented in the opposite direction as the other IMU. In various embodiments, the system takes the absolute value of the correlation coefficient and then checks to see how close that value is to one.

Another way to measure similarity between waveforms is to calculate a cross-correlation signal, and then look for a large amplitude peak in the cross-correlation signal. A cross-correlation signal is a measure of similarity of two series as a function of the displacement of one relative to another. An attractive feature of this method is that it is time invariant.

Another way to measure similarity between waveforms is to calculate the absolute error between the two signals and use that information to determine similarity. In one example, for each value or select values of the x-axis, the value for the y-axis for the internal IMU is subtracted from the value of the y-axis for the external IMU or vice-versa. Then the absolute value is taken to obtain the absolute error.

Another way to measure similarity between waveforms is to calculate the relative error between the two signals and use that information to determine similarity. In one example, for each value or many values of the x-axis, the value for the y-axis for the internal IMU is subtracted from the value of the y-axis for the external IMU or vice-versa. Then the resulting value is divided by one of the values of the y-axis. Then the absolute value is taken to obtain a value for the relative error.

An additional option for comparing two waveforms is to identify the times when specific peak amplitudes occur on the internal IMU and the external IMU. The difference between those times can be calculated. If the difference is below or at a difference threshold, then the signals are considered to match and authorized access is permitted. For example, the difference threshold may be 0.3 seconds or less, 0.5 seconds or less, 1 second or less, 2 seconds or less, or other values.

Determination if Access Key is Valid

After the comparison step, the system determines if the comparison indicates that an access key is valid at step 324 depending on the degree of closeness found during the comparison step.

In some examples, a correlation coefficient is calculated to determine the degree closeness during the comparison step and the comparison is deemed sufficiently close to permit second level communication depending on the value of the correlation coefficient. In various examples, an absolute value of the correlation coefficient ranges from zero to one, where one indicates a perfect match. In various examples, second level communication is permitted if the absolute value of the correlation coefficient is 0.5 or greater, 0.6 or greater, 0.7 or greater, 0.8 or greater, or 0.9 or greater.

Various examples where the IMD performs the comparison and determination step will now be described. The IMD can derive data from the internal IMU signal, such as the time of a first tap or a tap amplitude, and the external device can derive that same data from the external IMU signal. The external device sends the derived data to the IMD. The IMD compares the data derived by the IMD to the data derived by the external device. If the comparison indicates sufficient closeness, then the IMD permits a second level of communication. The data derived by the external device based on the external IMU signal serves as an access key that is compared to an access key standard generated by the IMD based on the internal IMD signal.

Second Level Communication

If the comparison step indicates a sufficient match, then the IMD starts an authorized second level of communication at step 326. If the comparison step indicates an insufficient match, then the second level of communication with the IMD is not permitted and is not initiated at step 328. Examples of second level of communication include transmission or receipt of secure data, patient data, instructions, commands, software updates, firmware updates, or a combination of these.

In some examples, the access key allows second level communication for a specified period of time or a specified number of queries, and then a new access key is provided to authorize further second level communication. Examples of the specified period of time or number of queries include about five minutes, about ten minutes, about one hour, about five queries, about ten queries, or queries up to a specific data size.

Synchronization and Fiducials

In various aspects, the data processing system includes computer instructions stored in memory to synchronize the internal IMU signal and the external IMU signal. One way to synchronize is to compare a timestamp of the internal IMU signal to a timestamp of the external IMU signal. The system may include a clock, such as a global high resolution clock to provide the timestamp.

In one example, when the external device and IMD start the authentication process with a first level communication, a first device, either the external device or the IMD, can send a signal indicating a clock time to the other device. The receiving device can compare the received clock time to the receiving device's clock time. If the clock times match, then the devices are synchronized. If the clock times do not matched, the receiving device can record an offset time that is the difference between the receiving device's clock time and the received clock time. The offset time can be used to select a portion of the IMU signal of the receiving device that will be used for the authentication process.

In another example, the external device, IMD, or both communicate wirelessly with a high-resolution global clock or other time standard. The external device and the IMD may then set their own clocks to match the time standard.

In addition or alternatively, a fiducial comparison can be used to synchronize data from the IMU signals by comparing a fiducial from the internal IMU signal with a fiducial of the external IMU signal. As used herein, a fiducial is a fixed point for comparison. One example of a fiducial is a signal peak from the IMU signal. For example, an internal signal peak from the internal IMU can be an internal fiducial which can be compared with a signal peak from the external IMU signal serving as an external fiducial. A signal peak in a waveform in the internal IMU signal can be aligned with a signal peak in a waveform of the external IMU signal as a part of selecting portions of the waveform to compare, in order to increase the chance of selecting simultaneous portions of the waveforms.

IMU Signal Examples (FIGS. 4-8)

IMU signals and examples of data that can be derived from IMU signals will now be described with reference to FIGS. 4-8. In each of FIGS. 4-8, an external IMU signal is depicted with a solid line on the graph and an internal IMU signal is shown with a dotted line on the graph. The x-axis is time as measured by sequential samples taken by the IMUs at a frequency of 200 samples per second, or 200 Hertz (Hz). As a result, each sample is spaced apart in time by 5 milliseconds. The y-axis is the output reading from an IMU in Gravity (G), where one Gravity is 9.81 meters per second squared.

In the examples of FIGS. 4-8, the output of a particular axis of an accelerometer, such as the output of an x-axis accelerometer or the output from a y-axis accelerometer, is displayed on the graph. In addition or alternatively, the IMU signal used for comparison can be selected by the data processing system after reviewing the signal from each axis of an accelerometer, for example. In addition or alternatively, a combination of the data from different axes of an accelerometer, such as a combination of data from the x-, y-, and z-axis, can be used in the comparison step.

Depending on the orientation of the IMU sensor, the output of a particular axis of the accelerometer may provide the most insightful waveform. The orientation of an internal IMU of an IMD within the patient's body is an unknown factor affecting the internal IMU output. An IMD may be fixed in orientation upon implantation into the patient's body, but the IMD may migrate to a different position within the patient's body over time. In addition, the patient's body can be in many different orientations during the authorization process. For these and other reasons, it may be helpful to have the particular IMU signal used for comparison selected by the data processing system after reviewing the signal from each axis of an accelerometer.

Now referring to FIGS. 1-2, in one embodiment, the external device 116 includes a screen 140 and a housing 142. At the initiation of an authorization process, the screen 140 can display instructions or a speaker can broadcast audible instructions to a user seeking authorized access to place the external device on the patient's body, such as on the patient's chest. The screen 140 can provide instructions to tap the patient's body, such as the patient's chest or sternum, a specific number of times to create the tap signature waveform on the internal IMU output and the external IMU output.

In addition or in the alternative, in various examples, the external device can instruct the patient and the user desiring authorized access to conduct certain activity during the recording of the IMU signals, such as breathing in a pattern, walking in a pattern, jumping, sitting, bending, or other motions. Instructions can be provided via the external device using a screen of the external device, audio voice instructions using a speaker, or other methods.

Tap Sequence

Figure 4:
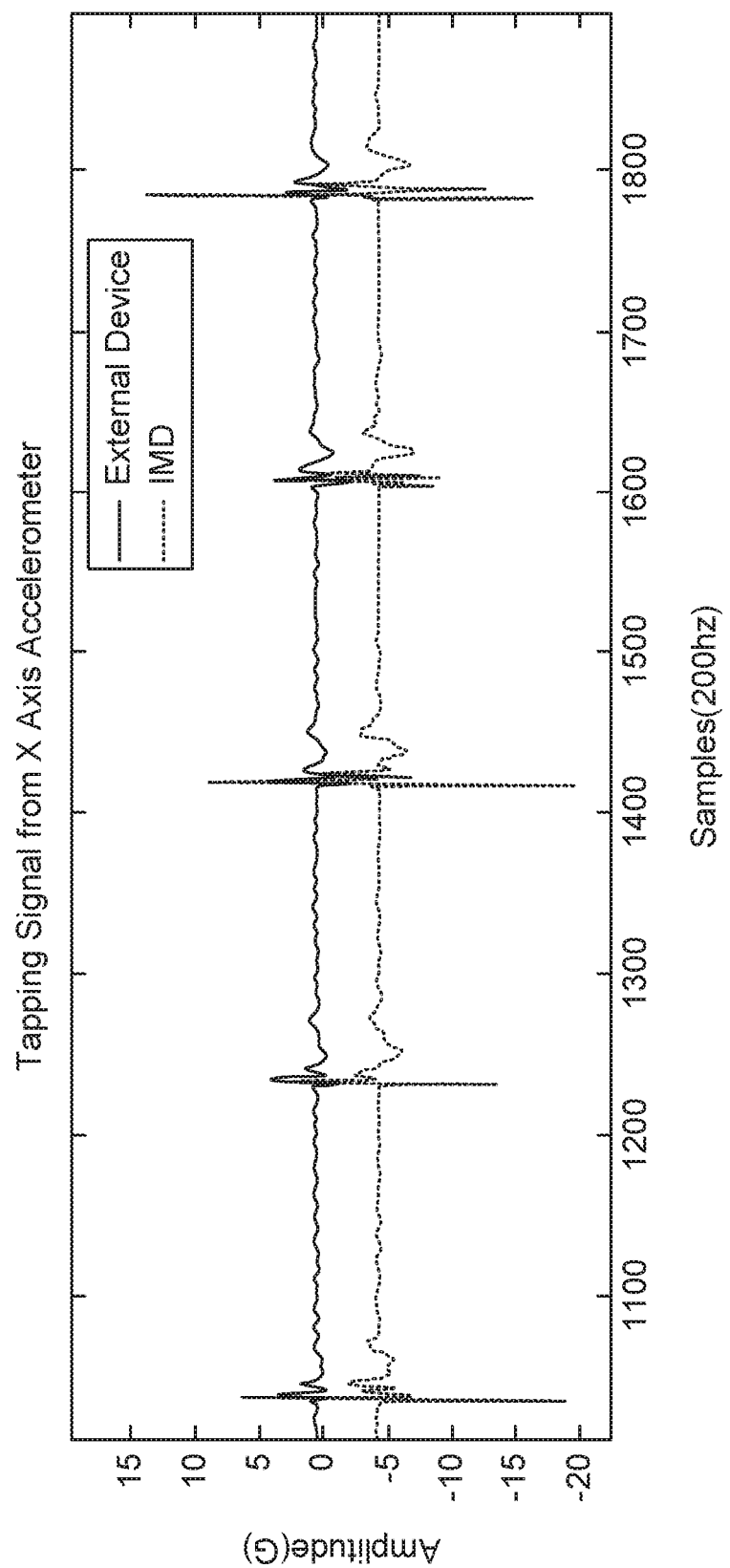
FIG. 4 is a graph of a tap sequence as detected at an internal IMU of an IMD and at an external IMU of an external device in accordance with various embodiments herein.

FIG. 4 is a graph of a tap signature as detected at an internal IMU of an IMD and at an external IMU of an external device in accordance with various embodiments herein. The output shown in FIG. 4 was measured by an x-axis accelerometer of the external IMU and the internal IMU. In the example of FIG. 4, five taps were recorded during about 10 seconds.

To produce the IMU signals shown in FIG. 4, an IMD having an internal IMU was attached to a subject's chest externally using an adhesive. A cellular phone having an external IMU was then placed against the subject's chest in very close proximity to the implant. Then, the subject tapped the chest repeatedly in a location of the chest very close to the IMD.

An authentication process using a tapping sequence can also be performed with the IMD and external device laying on a surface, such as a table, if it is helpful for the authentication process to occur outside of a patient's body. For example, authentication outside of a patient's body may be desirable to enabling high-security communication for a software update before implanting the IMD in the patient.

In various examples, the system calculates the time that passes between one or more taps as indicated using the waveforms from the internal IMU and the external IMU. This option has the advantage of not requiring a precise time synchronization step. In addition or in the alternative, other aspects of the two waveforms can be compared, including the morphology of the waveforms or the number of times the waveforms exceeds a particular minimum amplitude during a time period.

Heart Sound Waveform

Figure 5:
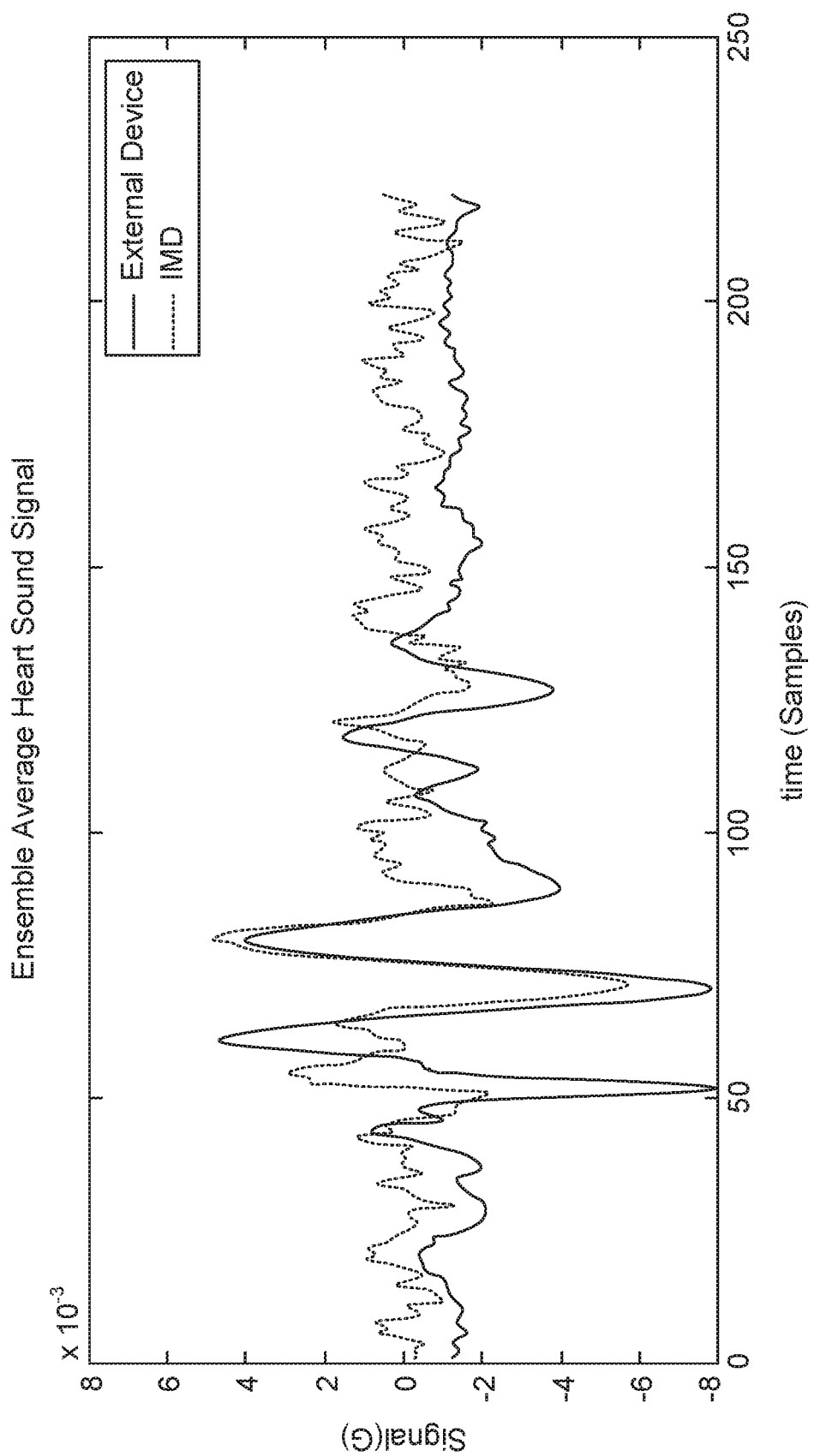
FIG. 5 is a graph of a heart sound signal as detected at an internal IMU of an IMD and at an external IMU of an external device in accordance with various embodiments herein.

FIG. 5 is a graph of an ensemble average of a heart sound signal as detected at an internal IMU of an IMD and at an external IMU of an external device in accordance with various embodiments herein. A heart beat signal of a particular patient is a repeating and unique signature each time the heart contracts. The first peak in the waveform is the S1 heart sound, while the second peak in the waveform is the S2 heart sound. The particular waveform is affected by a particular patient's anatomy, such as the size, structure and performance of the patient's heart. As a result, heart sound signals are highly variable and difficult to predict between different patients.

To create the ensemble average, several heart sound waveforms of the output of an IMU, such as from a specific axis of an IMU, over the course of time of one heartbeat are selected and are averaged. The course of time of each heartbeat is around one second. In various examples, about 15, about 16, at least 10, or at most 20 waveforms are averaged to create the ensemble average. To produce the IMU signals shown in FIG. 5, an IMD having an internal IMU was attached to a subject's chest externally using an adhesive. A cellular phone having an external IMU was then placed against the subject's chest in very close proximity to the implant. Then, the external IMU and internal IMU recorded the heart sound signal of the patient.

After creating an internal ensemble average from the internal IMU and an external ensemble average from the external IMU, a correlation coefficient is calculated to quantify the level of similarity between the two ensemble average waveforms, in various examples.

A variety of techniques can be used to compare a repeating signature of heart sounds. Exemplary techniques are described in commonly owned U.S. patent application Ser. No. 16/113,144, US20190083041, entitled "MULTICHANNEL HEART SOUND DETECTION," pending, filed Aug. 27, 2018 and Ser. No. 62/787,911, entitled "HEART SOUND MEASUREMENT USING MOBILE DEVICES," pending, filed Jan. 3, 2019, the disclosures of which are incorporated herein by reference.

In addition or in the alternatives, a patient's heart rate or a patient's heart rate variability can be calculated based on the IMU output, and can be compared between the internal and external IMU data.

Activity

Figure 6:
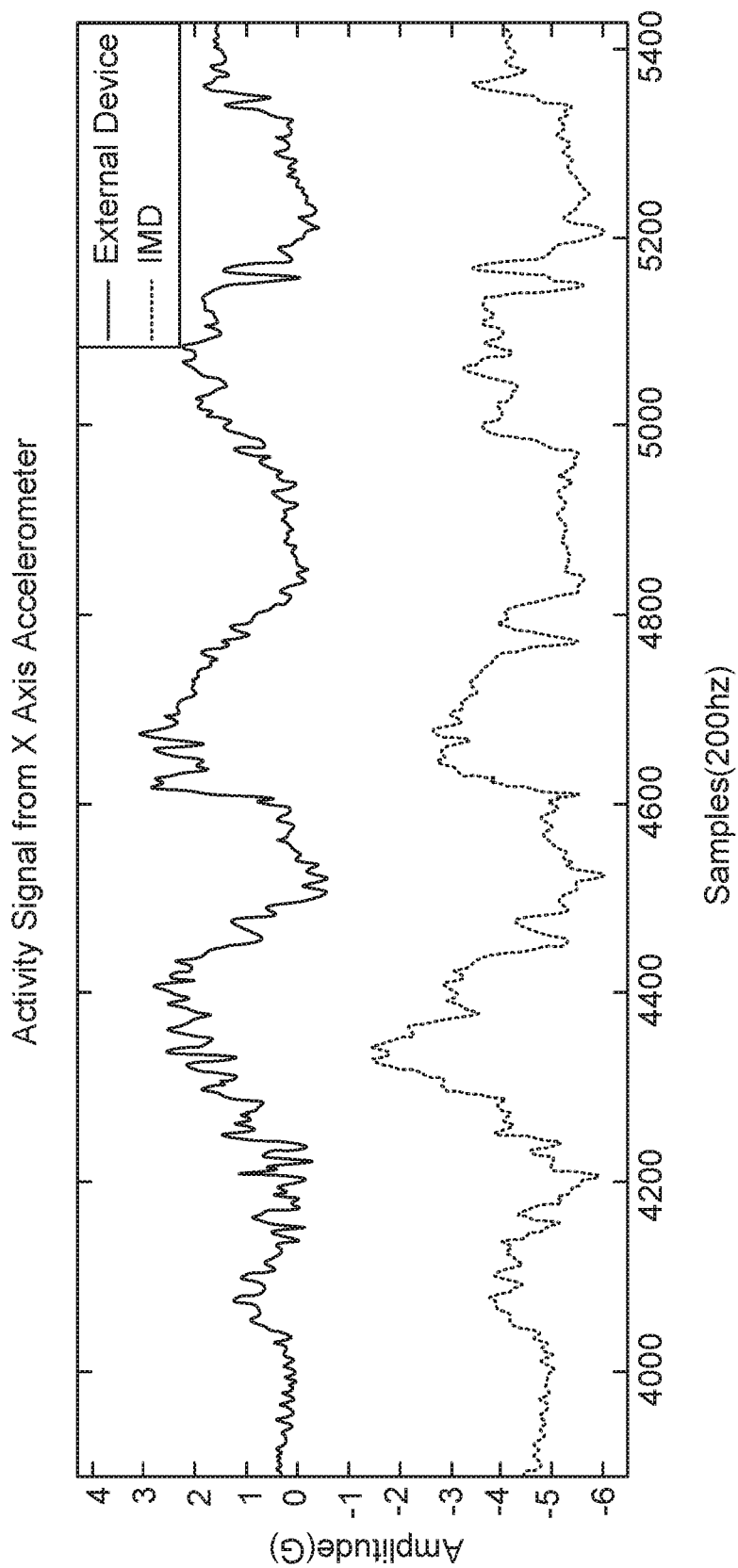
FIG. 6 is a graph of an activity signal as detected at an internal IMU of an IMD and at an external IMU of an external device in accordance with various embodiments herein.

FIG. 6 is a graph of an activity signal as detected at an x-axis accelerometer of an internal IMU of an IMD and at an x-axis accelerometer of an external IMU of an external device in accordance with various embodiments herein. During the recording of the signals shown in FIG. 6, an IMD having an internal IMU was attached to a subject's chest externally using an adhesive. A cellular phone having an external IMU was then placed against the subject's chest in very close proximity to the implant. Then, the subject walked in a circle while the two IMUs recorded the signal. A correlation coefficient between the two waveforms shown in FIG. 6 is about 0.8. The data shown in FIG. 6 was recorded over a time frame of about 7.5 seconds.

Respiration

Figure 7:
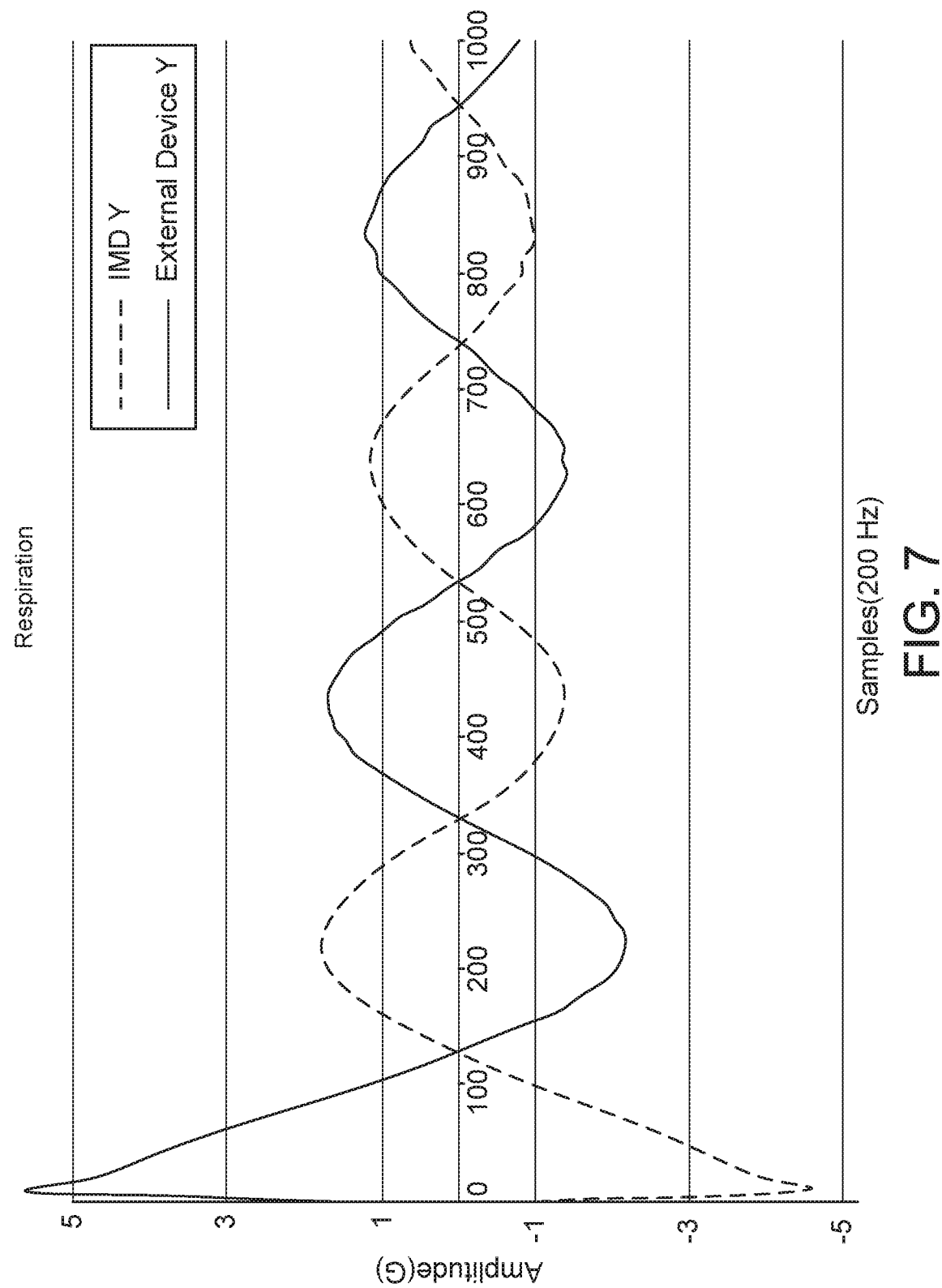
FIG. 7 is a graph of a respiration signal as detected at an internal IMU of an IMD and at an external IMU of an external device in accordance with various embodiments herein.

FIG. 7 is a graph of a respiration signal as detected at an internal IMU of an IMD and at an external IMU of an external device in accordance with various embodiments herein. The signals from the IMUs shown in FIG. 7 are from a y-axis accelerometer and indicate fast breathing of about four breaths during about 5 seconds.

To produce the IMU signals shown in FIG. 7, an IMD having an internal IMU was attached to a subject's chest externally using an adhesive. A cellular phone having an external IMU was then placed against the subject's chest in very close proximity to the implant. Then, the external IMU and internal IMU recorded the respiration signal while the subject performed faster-than-normal breathing.

To make the respiration signal more apparent and distinguishable from the heart sounds signal, a low pass filter can be applied to the signal. A correlation coefficient between the two signals of FIG. 7 is 0.9.

In addition or in the alternative, a zero-crossing algorithm can be used to detect the number of breaths during the time period of recording the IMU signals. The number of breaths during the recording period can be compared between the data from the external IMU and the internal IMU, in various examples.

Posture

Figure 8:
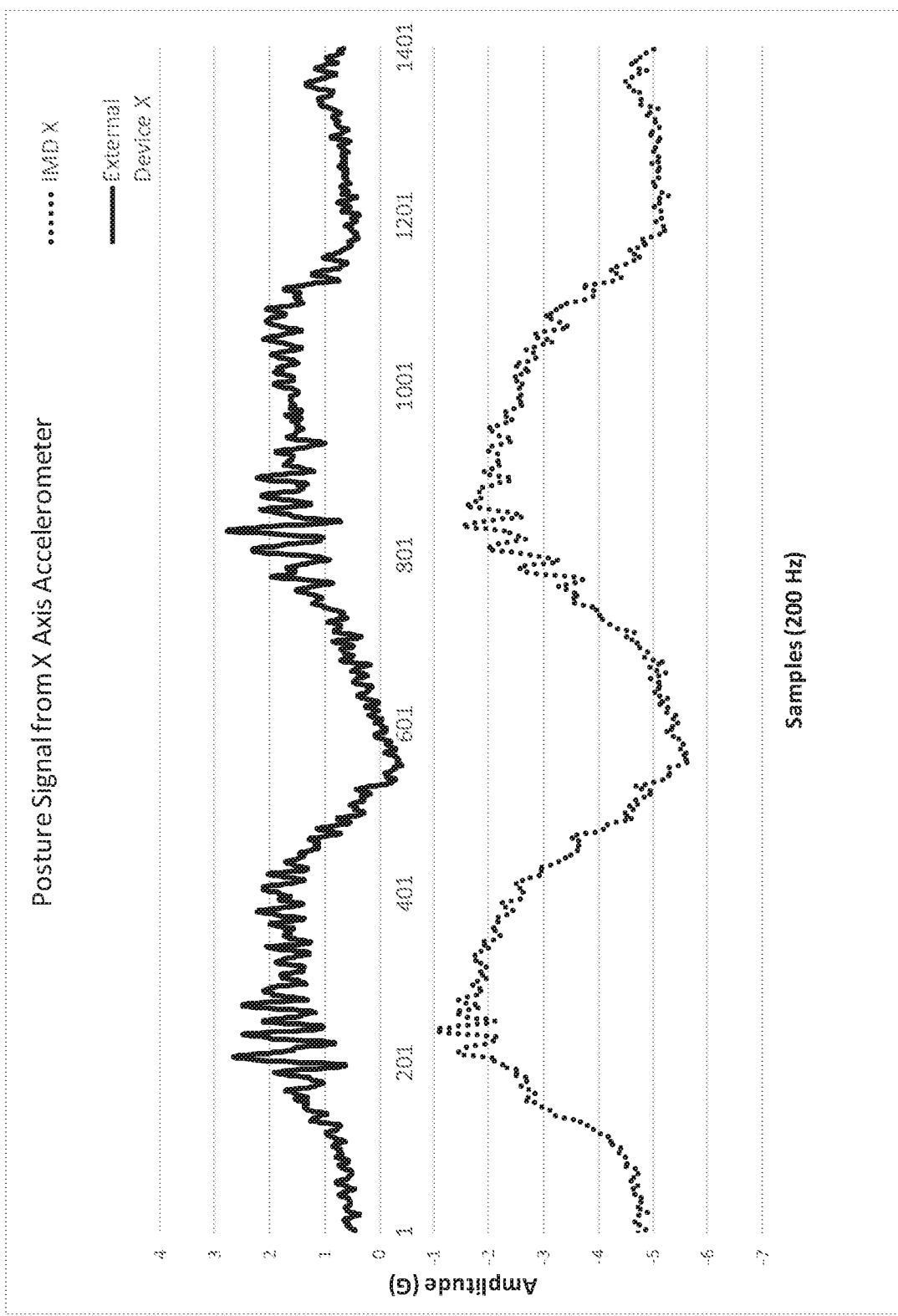
FIG. 8 is a graph of posture data as detected at an internal IMU of an IMD and at an external IMU of an external device in accordance with various embodiments herein.

FIG. 8 is a graph of posture data as detected at an internal IMU of an IMD and at an external IMU of an external device in accordance with various embodiments herein. The signals of FIG. 8 are from an x-axis accelerometer of the IMD and of the external device recorded. To produce the IMU signals shown in FIG. 8, the IMD was attached to a subject's chest externally using an adhesive. A cellular phone having the external IMU was then placed against the subject's chest in very close proximity to the implant. Then the signals were recorded while the subject spun in a swivel chair. The correlation coefficient between the signals is about 0.8.

In various examples, the patient can be instructed to lean forward and back or change their posture in another way during the recording of the IMU signals.

Instead of comparing data from the IMU signals of a single axis of an accelerometer, data from three axes of an accelerometer can be used to great a posture trajectory that is compared.

IMU and IMU Signal

An IMU is a device that is capable of measuring vibrations, movement or rotation. An IMU may include one or more accelerometers, gyroscopes, or magnetometers. Linear acceleration may be detected by one or more accelerometers. Rotational rate may be detected by one or more gyroscopes. A heading reference may be provided by a magnetometer. An IMU may include an accelerometer, a gyroscope, or a magnetometer for each axis, such as for the X-axis, Y-axis and Z-axis, or for pitch, roll and yaw. An accelerometer often measures acceleration of a body by using piezoresistive, piezoelectric or capacitive components to generate or modify an electrical signal based on mechanical motion. It is also possible to determine acceleration by the location of a heat bubble generated by a heater and measured with thermistors.

There are many options for how an IMU signal can be processed to arrive at an access key for authorizing secure communication. The IMU signal itself can be the access key. The access key can be a value or code generated using a portion of the IMU signal.

Figure 9:
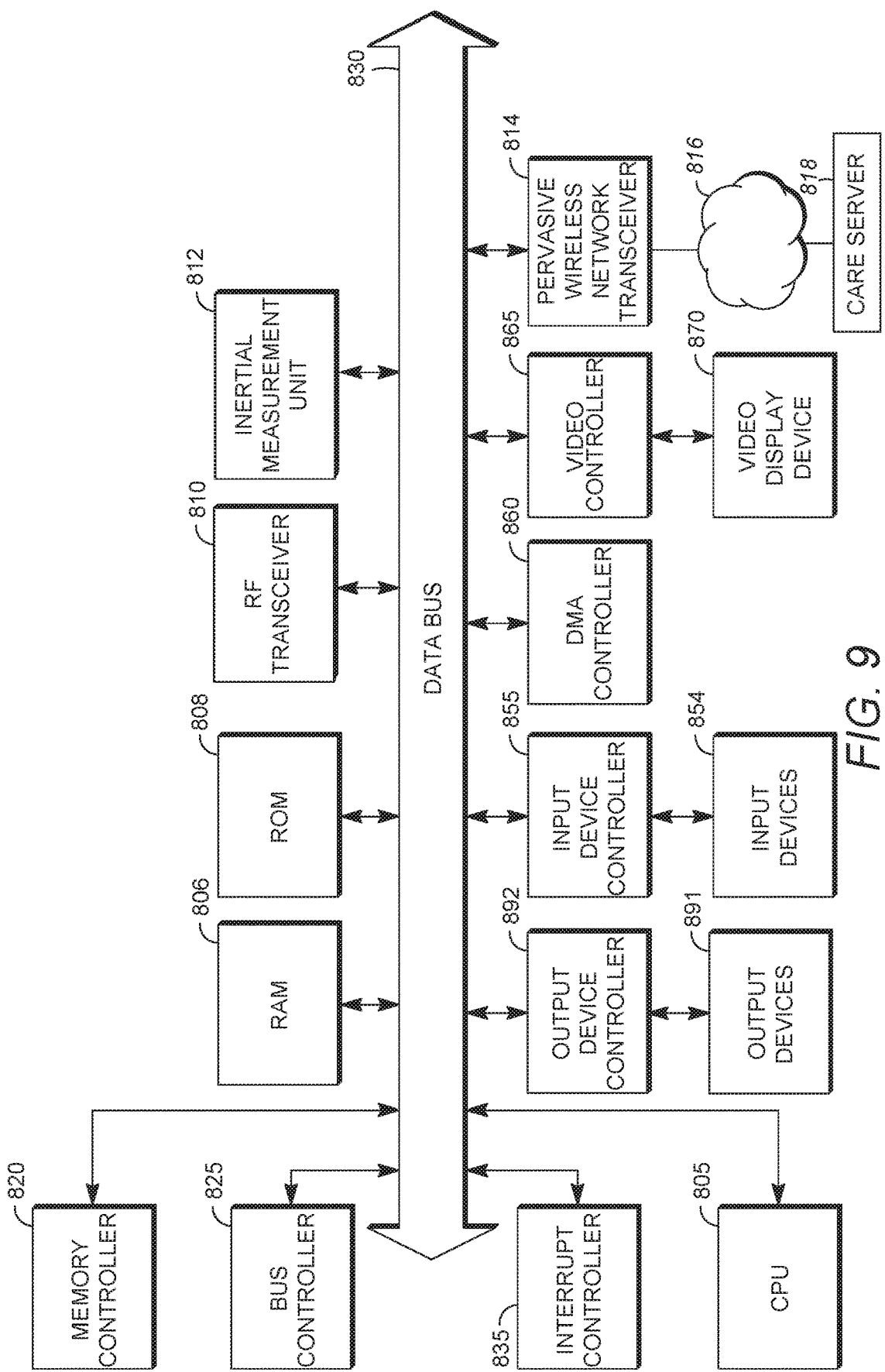
FIG. 9 is a schematic diagram of an implementation of the components of an external device in accordance with various embodiments.

External Device (FIG. 9)

FIG. 1 includes a front view of an external device 116, in the form of a cellular phone or smart phone, but many other options are possible. The external device 116 may be an IMD communicator device or tablet-style computer, for example. Alternatively, the external device may take the form of a wearable device or a watch-style device. Alternatively, the external device may take the form of an IMD programmer, a ruggedized laptop computer, a laptop computer, a desktop computer, a tablet computer, or another configuration. In some examples, an external device may be sized to be placed in contact with a patient's body, similar to the size of a smart phone.

In some examples, such as if the external device has a larger form like a laptop or desktop computer, an external device includes an extension portion having a body contact surface that is sized to be placed in contact with a patient's body. The extension portion may be easily attachable and detachable from an external device housing. The extension portion may be connected to a housing of the external device housing by a flexible cord or may communicate wirelessly with the external device.

In one embodiment, the external device 116 includes a screen 140, such as a touch screen, and a housing 142. The external device can include a camera, one or more speakers, and a microphone. In other embodiments, the external device 116 includes other user input devices such as a keyboard and a mouse.

In one embodiment, the external device 116 is configured for portability by a user, ease of placement on the patient's body, or both. For example, in one embodiment, the weight of the external device 116 is less than one kilogram. For example, in one embodiment, the weight of the external device 116 is less than 500 grams. In another embodiment, the weight of the external device 116 is less than 200 grams. In addition or alternatively, the external device 116 has a diagonal, corner-to-corner dimension of 15 centimeters (cm) or less, 10 cm or less, 8 cm or less, 6 cm or less, or 4 cm or less. In one embodiment the external device 116 has a diagonal, corner-to-corner dimension of at least 1 cm, at least 2 cm, at least 6 cm, at least 8 cm, or at least 10 cm. In one embodiment, a power source of the external device 116 is contained within the housing 142.

FIG. 9 is a schematic diagram of an implementation of the components of an external device in accordance with various embodiments. The external device can include components common to many computing devices, including smart phones, such as a central processing unit (CPU) 805 or processor, which may include a conventional microprocessor, random access memory (RAM) 806 for temporary storage of information, and read only memory (ROM) 808 for permanent storage of information. RAM 806 and ROM 808 are examples of external device memory.

The external device also include an RF transceiver 812. In some embodiments, the external device includes a pervasive wireless network transceiver 814 for communicating with a care server 816. The care server 816 may be a remote server comprising a data processing system for carrying out steps of the authentication process described herein. The external device 118 may include other equipment for interfacing with a care server, such as an ethernet cable receptacle. The RF transceiver may also be configured for interfacing with the care service, such as via another device. The external device 116 may have a communication link to the care server. The communication link between the external device 116 and the care server may be via phone lines, a wired network, the Internet 818, a pervasive wireless network, or any other data connection.

Generally, a pervasive wireless communication network is a communications network that can be used to directly communicate with a host computer without the need for a repeater device. A pervasive network includes those networks that are sufficiently prevalent or dispersed that an average person in the U.S. would be within range of interfacing with the network at some point during a normal daily routine. A pervasive wireless network typically has a relatively broad effective geographic span. There are many different usable pervasive wireless communication networks. One example is a wireless telephone network, such as a cellular telephone network. Other example embodiments of a pervasive wireless communication network include a wireless pager network, wireless wide area networks (WAN), such as those installed in certain public places like coffee shops, airports, schools, or municipalities, and wireless local area networks (LAN) including those following the standards set forth by the Institute for Electrical and Electronic Engineers (IEEE) in Standards 802.11 (b) and (g).

The external device 116 can also be used when it is not in communication with an IMD device, but is only in communication with the care server 132. In some examples, the external device 116 can also be used when it is not in communication with the care server 132, but is only in communication with an IMD.

In some embodiments, an external device is also a programmer of an IMD. As used herein, the term programmer refers to a device that programs IMDs and records data from IMDs. A programmer may also allow monitoring of the implanted device.

A memory controller 820 is provided for controlling system RAM 810. A bus controller 825 is provided for controlling data bus 830, and an interrupt controller 835 is used for receiving and processing various interrupt signals from the other system components.

Mass storage (not shown) can be provided in a variety of ways, such as by a solid state drive, a diskette drive, a CD-ROM drive, a hard disk drive, or other storage options. User input to the interface device system may be provided by a number of devices. For example, input devices 854 such as a keyboard and mouse can connect to bus 830 by input device controller 855. DMA controller 860 is provided for performing direct memory access to system RAM 806. A visual display is generated by a video controller 865 or video output, which controls video display 870. In addition to the visual display, the interface device may include other components for communicating with a user, such as speakers. For example, output devices 891 such as speakers can connect to bus 830 by output device controller 892.

The system can also include a telemetry interface or telemetry circuit which allows the system to interface and exchange data with an implantable medical device. In some examples, the telemetry interface is capable of inductive communication with the IMD, in some cases using an inductive wand. In some embodiments, the external device does not include hardware for inductive communication such as an inductive wand. A pattern recognition analysis module, a seeding module, parameter interaction module, pace timing optimization module and combinations thereof can be present in the interface device in different embodiments.

IMD (FIG. 10)

Figure 10:
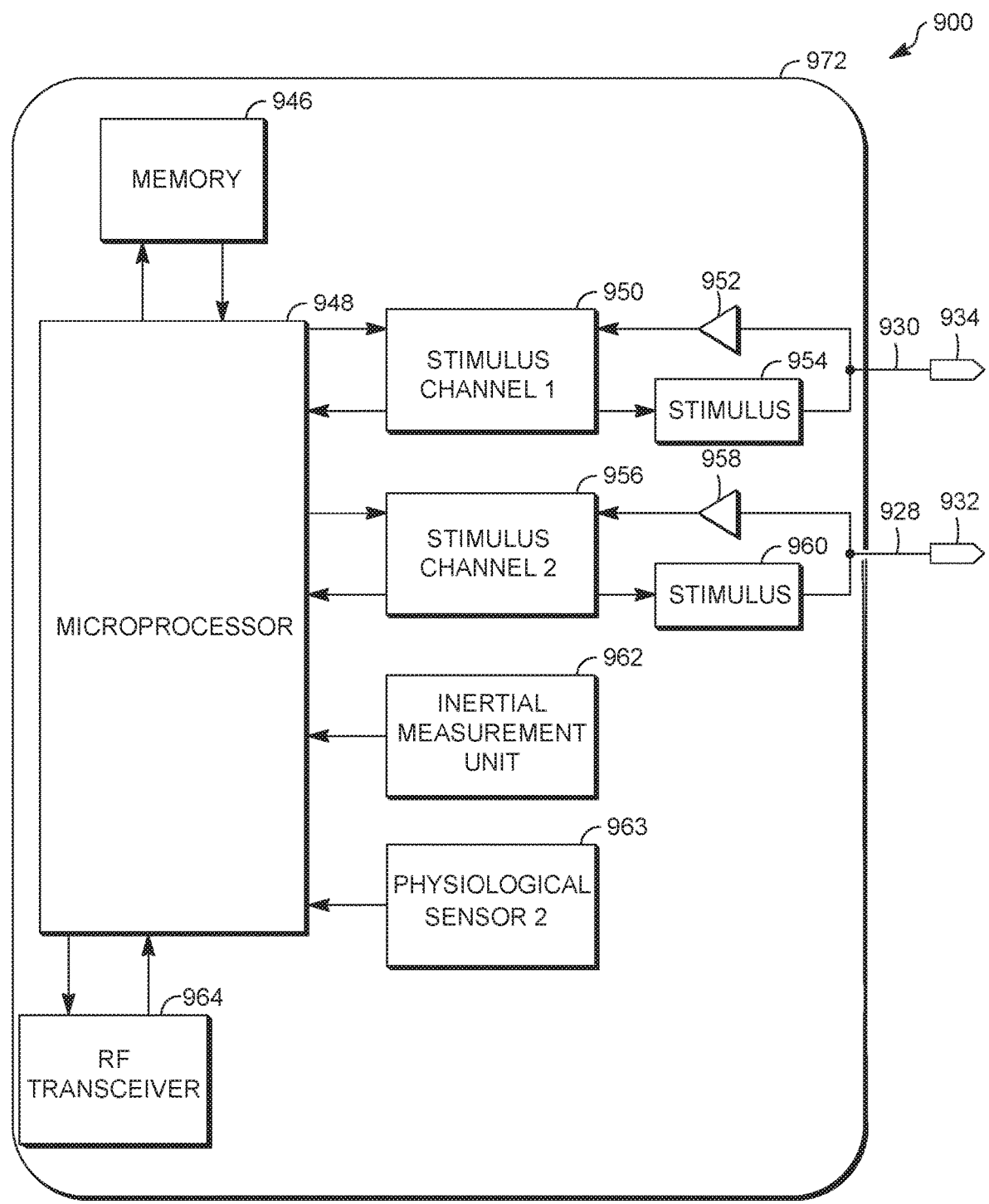
FIG. 10 is a schematic diagram of one example of an IMD in accordance with various embodiments.

FIG. 10 is a schematic diagram of one example of an IMD in accordance with various embodiments. The IMD 110 is capable of being implanted into a patient's body 102. One example of an IMD 110 is a cardiac IMD, which may include leads and be located near the patient's heart. Examples of IMDs 110 include, without limitation, a cardiac device, a pacemaker, a defibrillator, a cardiac resynchronization therapy (CRT) device, a single chamber implantable cardioverter defibrillator (ICD), a dual chamber ICD, a cardiac resynchronization therapy defibrillator (CRT-D), an implantable cardiac monitor (ICM), a leadless cardiac pacemaker (LCP), a subcutaneous implantable cardiac device (SICD), an insulin pump, a loop recorder, a neuro-stimulator, a physiological sensor, a glucose meter, or a combination of such devices.

Referring now to FIG. 10, some components of an exemplary implantable system 900 are schematically illustrated. The implantable system 900 can include an IMD 972 coupled to one or more stimulation leads 928 and 930. The IMD 972 can also include an inertial measurement unit (IMU) 962, a second physiological sensor 963, and one or more additional sensors. Examples of physiological sensors are electrodes, a pressure sensor, impedance sensor and others. In some examples, the IMD 972 does not include stimulation leads 928 and 930. In some examples, the IMD 972 includes only IMU 962 and does not include second physiological sensor. In some examples, the IMD 972 includes in two IMUs or three IMUs. Each IMU may be designed to measure a different axis of movement.

An RF transceiver 964 is provided for communicating with the external device in an RF communication mode.

The IMD can include a microprocessor 948 (or processor) that communicates with a memory 946 via a bidirectional data bus. The memory 946 typically comprises ROM or RAM for program storage and RAM for data storage. The IMD can be configured to execute various operations such as processing of signals and execution of methods as described herein.

The IMD can include first sensing and pacing channels comprising sensing amplifier 952, output circuit 954, and a stimulus channel 1 interface 950 which communicates bi-directionally with a port of microprocessor 948. The first sensing and pacing channel can be in communication with stimulation lead 930 and electrode 934. In one example, the first sensing and pacing channel is a ventricular sensing and pacing channel. The IMD can include second sensing and pacing channels comprising sensing amplifier 958, output circuit 960, and a stimulus channel 2 interface 956 which communicates bi-directionally with a port of microprocessor 948. The atrial sensing and pacing channel can be in communication with stimulation lead 928 and electrode 932. In one example, the second sensing and pacing channel is a atrial sensing and pacing channel. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

A seeding module, parameter interaction module, pace timing optimization module and combinations thereof can be present in the device in different embodiments.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A system for authenticating communication between an implantable medical device (IMD) for implantation in a patient and an external device, the system comprising:
   an IMD capable of being implanted into a patient's body, the IMD comprising:
      a wireless communication module, and
      an internal inertial measurement unit (IMU) capable of measuring vibrations, movement, or rotation,
      wherein the IMD is configured to record an internal IMU signal from the internal IMU;
   an external device located externally to the patient's body comprising:
      a wireless communication module, and
      an external IMU capable of measuring vibrations, movement, or rotation,
      wherein the external device is configured to record an external IMU signal from the external IMU; and
   a data processing system comprising computer instructions stored in memory to:
      receive a first level communication comprising the internal IMU signal, the external IMU signal, or both,
      compare data from the internal IMU signal with data from the external IMU signal, and
      authorize a second level communication based on results of the comparison step.

2. The system of claim 1 wherein the data processing system further comprises computer instructions stored in memory to synchronize the internal IMU signal and the external IMU signal.

3. The system of claim 2 wherein synchronizing further comprises comparing a timestamp of the internal IMU signal to a timestamp of the external IMU signal.

4. The system of claim 2 wherein synchronizing further comprises comparing a fiducial from the internal IMU signal with a fiducial of the external IMU signal.

5. The system of claim 4 where the fiducial from the internal IMU signal is a first signal peak and the fiducial from the external IMU signal is a second signal peak.

6. The system of claim 1 wherein the data processing system is:
   located in the IMD and receives the external IMU;
   located in the external device and receives the internal IMU; or
   located in an external server and receives the internal IMU and the external IMU.

7. The system of claim 1 wherein the external device is a mobile device, a cellular telephone, a wearable device, or a combination of these.

8. The system of claim 1 wherein the internal IMU comprises a first accelerometer, a first gyroscope, or a first magnetometer and wherein the external IMU comprises a second accelerometer, a second gyroscope, or a second magnetometer.

9. The system of claim 1 wherein the comparison step comprises:
   comparing the internal IMU signal with the external IMU signal, or
   comparing data derived from internal IMU signal with data derived from the external IMU signal.

10. The system of claim 1 wherein the data processing system derives a heart sound signal, a heart rate signal, a posture signal, a respiration signal, an external device vibration signal, or a tap signal from the internal IMU signal and the external IMU signal.

11. The system of claim 1 wherein the second level of communication comprises secure data, patient data, instructions, commands, software updates, firmware updates, or a combination of these.

12. A method for authenticating communication between an implantable medical device (IMD) and an external device, wherein the IMD is capable of being implanted into a patient's body and comprises a wireless communication module and an internal inertial measurement unit (IMU), wherein the external device is located externally to the patient's body and comprises a wireless communication module, and an external IMU, the method comprising:
   recording an internal IMU signal from the internal IMU;
   recording an external IMU signal from the external IMU;
   receiving a first level communication comprising the internal IMU signal, the external IMU signal, or both;
   comparing data from the internal IMU signal with data from the external IMU signal; and
   authorizing a second level communication based on results of the comparison step.

13. The method of claim 12 wherein the IMD is implanted in the patient's body and further comprising placing the external device in contact with the patient's body.

14. The method of claim 12 further comprising initiating a second level communication session by sending a request from the external device to the IMD.

15. The method of claim 12 further comprising synchronizing the internal IMU signal and the external IMU signal.

16. The method of claim 15 wherein synchronizing further comprises:
   comparing a first timestamp of the internal IMU signal to a second timestamp of the external IMU signal,
   comparing a first fiducial from the internal IMU signal with a second fiducial of the external IMU signal, or
   comparing a first signal peak from the internal IMU signal with a second signal peak from the external IMU signal.

17. The method of claim 12 wherein a data processing system performs the step of receiving and is:
   located in the IMD and receives the external IMU;
   located in the external device and receives the internal IMU; or
   located in an external server and receives the internal IMU and the external IMU.

18. The method of claim 12 wherein the step of comparing comprises:
   comparing the internal IMU signal with the external IMU signal, or
   comparing data derived from internal IMU signal with data derived from the external IMU signal.

19. The method of claim 12 further comprising deriving a heart sound signal, a heart rate signal, a posture signal, a respiration signal, an external device vibration signal, or a tap signal from the internal IMU signal and from the external IMU signal.

20. The method of claim 12 wherein after the second level of communication is authorized, sending secure data, patient data, instructions, commands, software updates, firmware updates, or a combination of these to or from the IMD.

* * * * *